US008890682B2

(12) United States Patent
Tounooka (10) Patent No.: US 8,890,682 B2
(45) Date of Patent: Nov. 18, 2014

(54) BLOOD GLUCOSE MEASURING DEVICE (71) Applicant: Terumo Kabushiki Kaisha, Shibuya-ku (JP)

(72) Inventor: Yuuya Tounooka, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/927,803

(22) Filed: Jun. 26, 2013

(65) Prior Publication Data
US 2013/0285807 A1 Oct. 31, 2013

Related U.S. Application Data (63) Continuation of application No. PCT/JP2011/006732, filed on Dec. 28, 2011.

(30) Foreign Application Priority Data

Dec. 28, 2010 (JP) .................................. 2010-293750

(51) Int. Cl.
*G08B 1/08* (2006.01)
*G06F 19/00* (2011.01)
*C12Q 1/54* (2006.01)
*A61B 5/00* (2006.01)
*G01N 27/327* (2006.01)
*A61B 5/1455* (2006.01)
*A61B 5/145* (2006.01)
*G06F 19/10* (2011.01)

(52) U.S. Cl.
CPC .......... *A61B 5/0004* (2013.01); *G06F 19/3406* (2013.01); *G06F 19/3456* (2013.01); *C12Q 1/54* (2013.01); *G01N 27/3274* (2013.01); *A61B 5/00* (2013.01); *A61B 5/1455* (2013.01); *A61B 5/14532* (2013.01); *G06F 19/10* (2013.01); *A61B 5/746* (2013.01)
USPC .................................................... 340/539.12

(58) Field of Classification Search
USPC .......... 340/539.1, 573.1, 572.1–572.9, 13.26; 600/365; 702/19, 179
See application file for complete search history.

(56) References Cited

U.S. PATENT DOCUMENTS 7,110,112 B2 * 9/2006 Uchida et al. .................. 356/364
8,626,453 B2 * 1/2014 Myoujou et al. ................ 702/31

(Continued)

FOREIGN PATENT DOCUMENTS

EP 1 728 470 A1 12/2006
JP 2003-159234 A 6/2003

(Continued)

OTHER PUBLICATIONS

International Search Report (PCT/ISA/210) issued on Mar. 13, 2012, by the Japanese Patent Office as the International Searching Authority for International Application No. PCT/EP2011/006732.

*Primary Examiner* — Phung Nguyen
(74) *Attorney, Agent, or Firm* — Buchanan Ingersoll & Rooney PC (57) ABSTRACT A blood glucose measuring instrument is configured to output guidance allowing a subject to take appropriate countermeasure. The blood glucose measuring instrument includes a first setting device for receiving a static limit value wirelessly transmitted from an authenticated external apparatus and setting the static limit value, storage for classifying and storing blood glucose level data acquired by a blood glucose measurement based on classification according to the measurement timing, a second setting device for calculating, using past blood glucose level data stored in classified groups in the storage, a distribution for each classified group and setting a dynamic limit value based on the calculated distribution, and a notifying device which compares blood glucose level data with the static limit value and the dynamic limit value for the classified group to which the blood glucose level data belongs to provide notification about a result of the comparison.

20 Claims, 8 Drawing Sheets (56) References Cited

U.S. PATENT DOCUMENTS

| | | | |
|---|---|---|---|
| 2004/0181132 A1* | 9/2004 | Rosenthal | 600/316 |
| 2005/0192491 A1 | 9/2005 | Cho et al. | |
| 2006/0277048 A1 | 12/2006 | Kintzig et al. | |
| 2011/0098600 A1* | 4/2011 | Matsumura et al. | 600/583 |
| 2011/0205064 A1* | 8/2011 | Strachan et al. | 340/573.1 |
| 2012/0172691 A1* | 7/2012 | Brauker et al. | 600/347 |
| 2014/0012511 A1* | 1/2014 | Mensinger et al. | 702/19 |

FOREIGN PATENT DOCUMENTS

| | | |
|---|---|---|
| JP | 2005-198790 A | 7/2005 |
| JP | 2005-237688 A | 9/2005 |
| JP | 4395146 B2 | 1/2010 |
| JP | 2010-236943 A | 10/2010 |

* cited by examiner

BLOOD GLUCOSE MEASURING DEVICE

CROSS REFERENCES TO RELATED APPLICATIONS

This application is a continuation of International Application No. PCT/2011/006732 filed on Dec. 1, 2011, and is based upon and claims the benefit of priority of Japanese Patent Application No. 2010-293750, filed on Dec. 28, 2010, the entire content of both of which is incorporated herein by reference.

TECHNICAL FIELD

The present invention generally relates to a blood glucose measuring instrument.

BACKGROUND DISCUSSION

A blood glucose measuring instrument is available which incorporates a voice outputting function for a visually-impaired subject, and so the subject can be notified by voice about blood glucose level data acquired by measurement.

However, an instrument in which a result of a measurement is outputted by voice can be problematic in that, if the subject fails to listen or the like, a suitable decision cannot be carried out. Further, even if the subject can correctly listen to the outputted voice, for example, in order to decide whether the measured blood glucose level is high or low in comparison with a normal blood glucose level of the subject himself or herself, the subject has to rely upon his/her own recollection of voice data listened to in the past, and so it may be difficult to carry out an accurate decision. Particularly, since the blood glucose level varies before and after a meal, a measurement result before a meal and a measurement result after a meal have to be stored individually by the subject himself or herself in order to accurately carry out the decision.

From the foregoing, it is preferable to configure a blood glucose measuring instrument such that it compares a measurement result with regard to a subject (who may have visual impairment) and a predetermined threshold value on the blood glucose measuring instrument and, when it is determined that the measurement result exceeds the threshold value, the measurement result can be outputted by voice together with a voice message representing that the measurement result exceeds the threshold value.

Against this background, in the field of blood glucose measuring instruments, an instrument has been proposed which functions to accumulate blood glucose level data acquired in the past by measurements, calculating appropriate threshold values for individual subjects by calculating an average value or the like and then, when the threshold value is exceeded, notifying the subject of this. Also an instrument has been proposed which can make a more precise decision by setting a threshold value separately for times before and after a meal or for individual time zones.

Japanese Patent Laid-Open No. 2003-159234, Japanese Patent Laid-Open No. 2005-237688 and Japanese Patent Laid-Open No. 2005-198790 disclose examples of known blood glucose measuring instruments.

SUMMARY

To a subject, it would be preferable for a blood glucose measuring instrument to be configured so that the instrument able is not only able to determine a tendency that a measurement result is high or low in comparison with a blood glucose level in a normal state of the subject himself or herself, but also so that when the measurement result is high, a decision about whether or not the subject should go to a hospital and be diagnosed by a doctor or the like (in short, a decision for allowing the subject to take an appropriate countermeasure) is carried out. This is because, if such a decision is carried out by the blood glucose measuring instrument, subjective judgment of the subject can be excluded.

In order for the blood glucose measuring instrument to rather precisely carry out such a judgment as just described, an appropriate threshold value determined by a specialist such as a doctor should be set for each subject.

On the other hand, from the standpoint of the doctor or the like (medical professional), it is convenient that if, when a patient is diagnosed, an appropriate threshold value based on a diagnosis result can be set for each patient and management of the blood glucose level can be carried out for each patient, for example like "if the blood glucose level of the patient A reaches the XX level, then it is necessary to diagnose the patient A again," then even in a case in which a variation occurs with a blood glucose level of a patient, appropriate treatment can be carried out for the patient immediately.

The blood glucose measuring instrument disclosed here can output guidance (verbal guidance) allowing a subject to take an appropriate countermeasure.

According to one aspect, a blood glucose measuring instrument comprises: a communication section configured to wirelessly communicate with an external apparatus operated by a medical professional; first setting means for setting a received static limit value, inputted by the medical professional at the external apparatus and transmitted wirelessly from the external apparatus to the blood glucose measuring instrument, as a first threshold value; storage means for storing blood glucose level data acquired by blood glucose measurement of a blood sample taken from a subject, including most recent blood glucose level data acquired by a most recent blood glucose measurement, with the storage means storing the blood glucose level data in one of several classified groups each representing a different measurement time period during which blood glucose level measurements were performed; and second setting means for calculating, using the blood glucose level data stored in the classified groups, a dynamic limit value of the blood glucose level data in each classified group and for setting the dynamic limit value as a second threshold value. Notification means compares the most recent blood glucose level data with both the first threshold value and the second threshold value of the classified group in which the most recent blood glucose level data is classified for providing notification about a result of the comparison of the most recent blood glucose level data with both the first threshold value and the second threshold value of the classified group in which the most recent blood glucose level data is classified.

According to another aspect, a blood glucose measuring instrument configured to produce voice output comprises: first setting means for receiving first threshold value information transmitted by wireless transmission from an external apparatus in accordance with a condition that the external apparatus has been authenticated and for setting the received first threshold value information as a first threshold value; storage means for classifying and storing blood glucose level data acquired by blood glucose measurement based on classification according to the measurement timing; second setting means for calculating, using the blood glucose level data stored in classified groups in the storage means, a distribution for each classified group and setting a second threshold value based on the calculated distribution; and notification means which compares the blood glucose level data acquired by the blood glucose measurement with the first threshold value and the second threshold value corresponding to the classified group to which the blood glucose level data belongs to notify output contents in accordance with a result of the comparison of the blood glucose level data acquired by the blood glucose measurement with the first threshold value and the second threshold value.

In accordance with another aspect, a method comprises: measuring a blood glucose level of a most recent blood sample acquired from a subject though use of a blood glucose measuring instrument; and comparing the measured blood glucose level of the most recent blood sample to a first threshold value, with the first threshold value being a value previously wirelessly received by the blood glucose measurement instrument from an external apparatus at which a medical professional inputted the first threshold value, and the blood glucose measurement instrument storing a plurality of past measured blood glucose levels in one of several classified groups, wherein each of the classified groups represents a different measurement time period during which blood glucose level measurements were performed, and with the measured blood glucose level of the most recent blood sample being classified in one of the classified groups which is the measurement time period during which blood glucose level measurement of the most recent blood sample was performed. The method also includes comparing the measured blood glucose level of the most recent blood sample to a second threshold value of the one classified group, with the second threshold value being calculated using the past measured blood glucose levels of the one classified group, and notifying the subject about a result of the comparison of the measured blood glucose level of the most recent blood sample to the first threshold value and the second threshold value.

Other features and aspects of the blood glucose measuring instrument and method disclosed here will become apparent from the following detailed description considered together with the accompanying drawings in which like features are designated by like reference numerals.

BRIEF DESCRIPTION OF DRAWINGS

The accompanying drawings are included in the specification and form a part of the disclosure here, exemplify a disclosed embodiment, and are used to disclose aspects and principle of the disclosure here together with the detailed description set forth below.

DETAILED DESCRIPTION

Embodiments of the blood glucose measuring instrument disclosed here are described below with reference to the accompanying drawings. Generally speaking, the embodiments of the blood glucose measuring instrument described below exhibit the following characteristics or aspects.

When a result of a measurement (blood glucose level data) is outputted by voice to a subject, output contents (voice message) representative of a result of a decision about the measurement result are also outputted.

The outputted decision result includes two kinds of information, including information representative of such a tendency that the measurement result is high or low in comparison with measurement results in a normal state of the subject, and information on which a decision from a medical point of view about the subject by a doctor or the like is reflected.

Regarding the former information, the blood glucose measuring instrument is configured such that a threshold value (an upper limit value, a lower limit value, or upper and lower limit values) is calculated dynamically using accumulated blood glucose data specific to the subject so that characteristics of the subject may be reflected, and such that the threshold value is calculated separately for timings before meals and after meals and for individual time zones (in short, in response to each measurement timing) so that a more appropriate threshold value may be obtained. In the following description, the threshold value information which varies dynamically is referred to as "dynamic limit value"

Concerning the latter information, the blood glucose measuring instrument is configured such that the threshold value is transmitted from a predetermined external apparatus by wireless communication and set in accordance with a condition of a predetermined authentication so that only a doctor or the like can set the threshold value, and a subject cannot change the threshold value. In the following description, the fixed threshold value information set by a doctor or the like using a predetermined external apparatus is referred to as "static limit value".

The following sets forth a detailed description of embodiments having the characteristics described above. It is to be noted that the invention is not limited to the following embodiments.

Outer Appearance Configuration of the Blood Glucose Measuring Instrument

Figure 1:
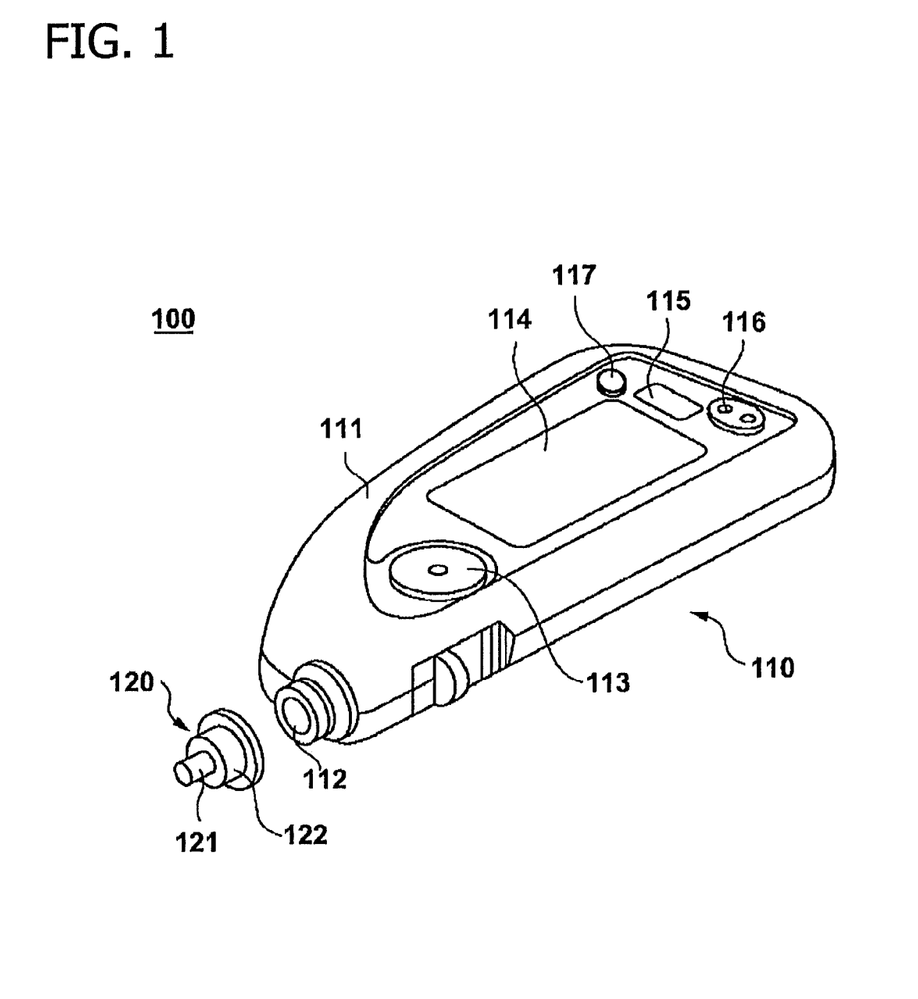
FIG. 1 is a perspective view of a blood glucose measuring instrument according to an embodiment disclosed by way of example here.

FIG. 1 illustrates the outer appearance of the blood glucose measuring instrument 100 according to one embodiment disclosed by way of example. As shown in FIG. 1, the blood glucose measuring instrument 100 includes a measuring instrument main body section 110, and a measuring chip 120 mounted on the measuring instrument main body section 110.

The measuring chip 120 retains a blood specimen (blood glucose specimen) and includes a holder 122 on which a narrow tube portion 121 is disposed. A test paper is defined or positioned in the inside of the holder 122.

A blood specimen is introduced into the narrow tube portion 121 from an end opening of the tube portion into the inside of the holder 122 by capillary action. The blood specimen introduced through the narrow tube portion 121 is absorbed by the test paper in the inside of the holder 122. The test paper is impregnated with coloring reagent which reacts with glucose to exhibit a color reaction.

The measuring instrument main body section 110 calculates a blood glucose level of the blood specimen retained by the measuring chip 120. In particular, two beams of light having different wavelengths are irradiated upon the test paper in which the blood specimen is absorbed to measure the intensity of reflected light to calculate a blood glucose level.

A measuring portion 112 which irradiates two beams of light having different wavelengths upon the test paper to measure the intensity of reflected light is disposed at an end of a housing 111 of the measuring instrument main body section 110. Further, a control section which controls the measuring portion 112 and executes various arithmetic operations for measurement light value data acquired by the measuring portion 112 is disposed in the inside of the housing 111.

The surface of the housing 111 is provided with a power supply switch 113 for inputting ON/OFF instruction to a power supply for supplying power to the blood glucose measuring instrument 100, a display section 114 for displaying blood glucose level data calculated by the control section or an internal state detected by the control section, a history call button 115 for calling blood glucose level data in the past calculated and stored by the control section and causing the blood value data to be displayed on the display section 114, a reproduction button 116 for outputting a voice message outputted by voice again, and an after-meal button 117 for inputting that the timing of the blood glucose measurement is a timing after a meal.

The voice outputting section for outputting calculated blood glucose level data by voice and outputting a result of a decision based on contrast between the blood glucose level data and a dynamic limit value or a static limit value as a voice message by voice is disposed on the back face side of the measuring instrument main body section 110.

Functional Configuration of the Blood Glucose Measuring Instrument

Figure 2:
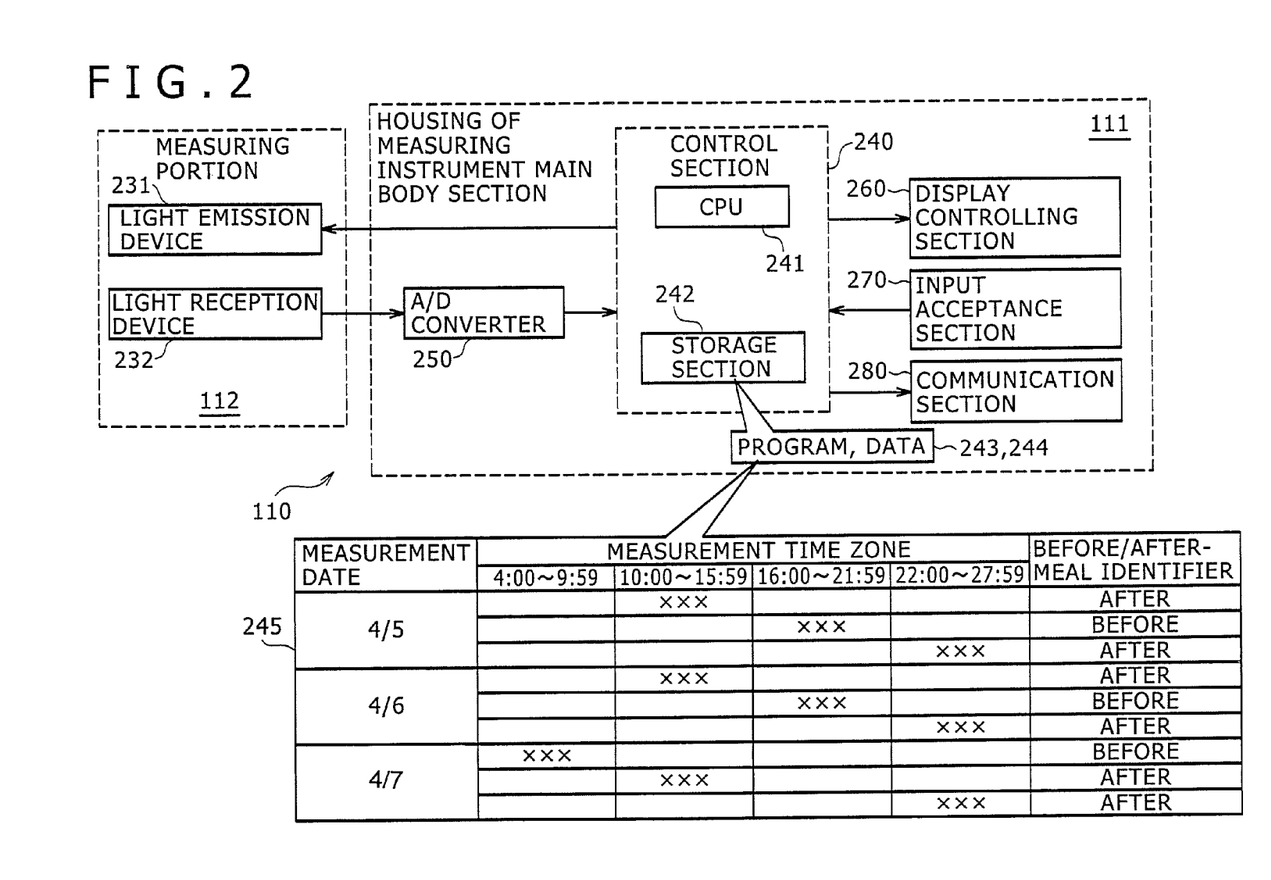
FIG. 2 is a schematic illustration of a functional configuration of a measuring instrument main body section of the blood glucose measuring instrument.

The functional configuration of the measuring instrument main body section 110 of the blood glucose measuring instrument 100 is illustrated in FIG. 2. A light emission device 231 and a light reception device 232 are disposed at the measuring portion 112 of the measuring instrument main body section 110. The light emission device 231 emits light based on a light emission instruction from a control section 240, and the light reception device 232 receives reflected light of the light irradiated upon the test paper by emission of light of the light emission device 231 to generate measurement light value data.

The control section 240, an A/D converter 250, a display controlling section 260, an input acceptance section 270 and a communication section 280 are disposed in the housing 111 of the measuring instrument main body section 110.

The A/D converter 250 carries out A/D conversion of measurement light value data generated by the light reception device 232 and inputs the A/D converted measurement light value data to the control section 240.

The control section 240 includes a CPU 241 and a storage section 242. Various programs 243 for implementing functions as the blood glucose measuring instrument 100 (including a program for calculating blood glucose level data based on measurement light value data inputted thereto through the A/D converter 250, a program for setting a static limit value and a dynamic limit value and a program for contrasting and deciding the calculated blood glucose level data with the static limit value and/or the dynamic limit value) and various data 244 (including the calculated blood glucose level data and the set static limit value and/or dynamic limit value) are stored in the storage section 242 and executed suitably by the CPU 241.

Blood glucose level data stored in the storage section 242 are classified for each measurement date and measurement time zone as illustrated in a table 245. Further, an identifier indicative of whether blood glucose measurement has been carried out before a meal or after a meal is associated with the blood glucose level data (in short, the blood glucose level data are classified according to the measurement timing).

The display controlling section 260 controls the display section 114 based on a displaying instruction from the control section 240 to display a predetermined screen image (a screen image for displaying calculated blood glucose level data or information indicative of an internal state of the control section 240). The input acceptance section 270 accepts an instruction from the power supply switch 113, history call button 115, reproduction button 116 or after-meal button 117 of FIG. 1 and transmits the accepted instruction to the control section 240.

On the communication section 280, a RFID tag for communicating with an RFID reader/writer connected to an information processing terminal handled by a doctor or the like in a hospital or the like in order to set a static limit value is disposed.

Static Limit Value Setting

Figure 3A:
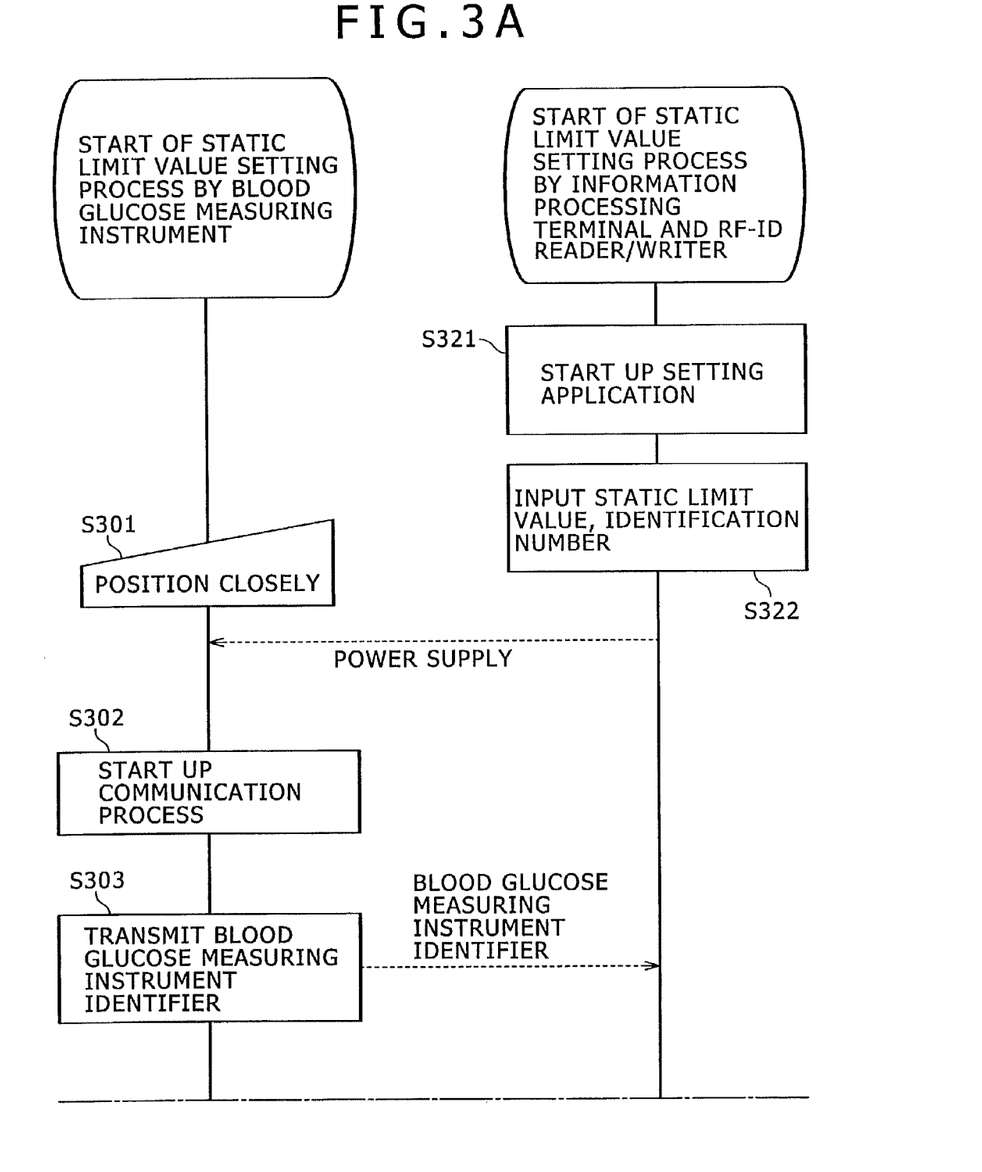
FIG. 3A illustrates a part of an operational routine of a static limit value setting process performed by the blood glucose measuring instrument.
Figure 3B:
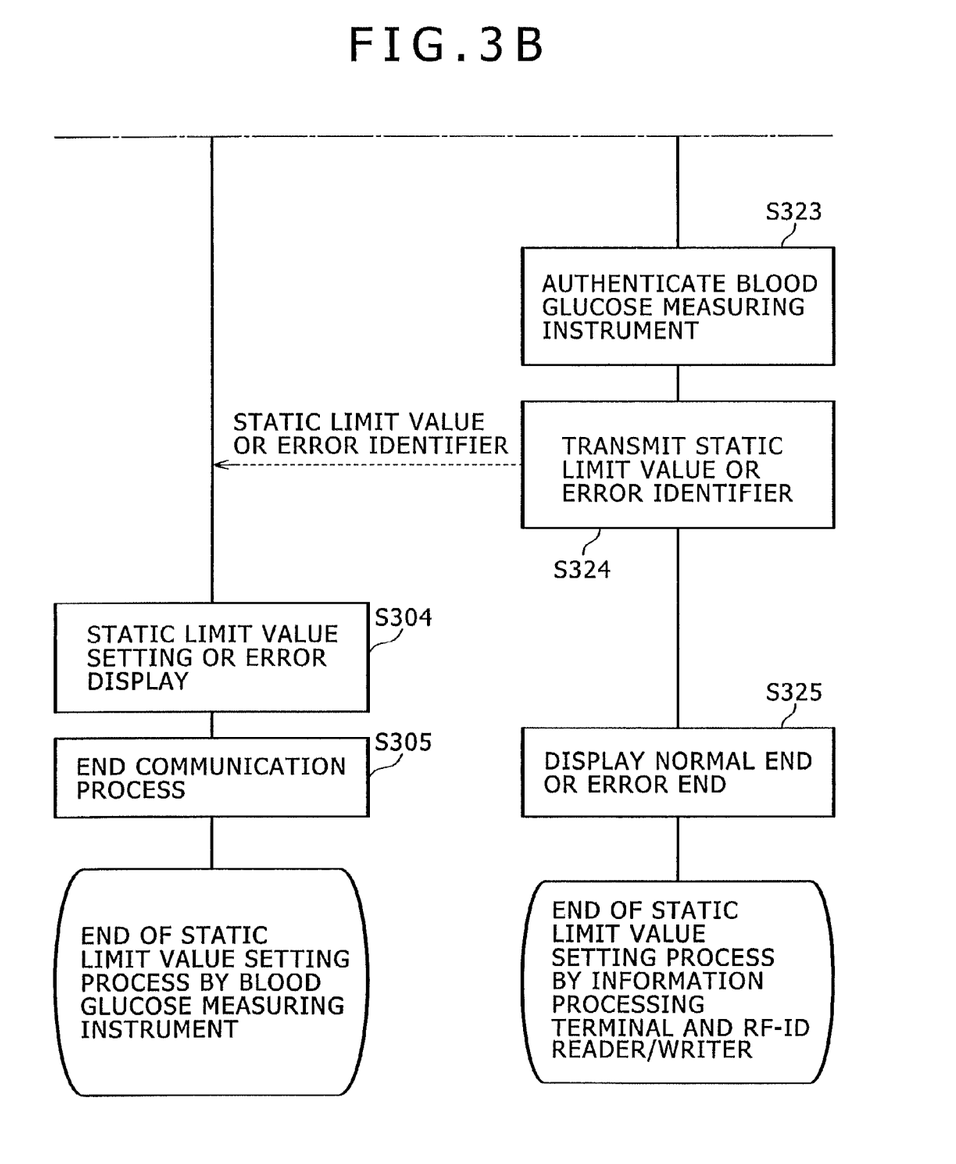
FIG. 3B illustrates another part of an operational routine of the static limit value setting process performed by the blood glucose measuring instrument.
Figure 4:
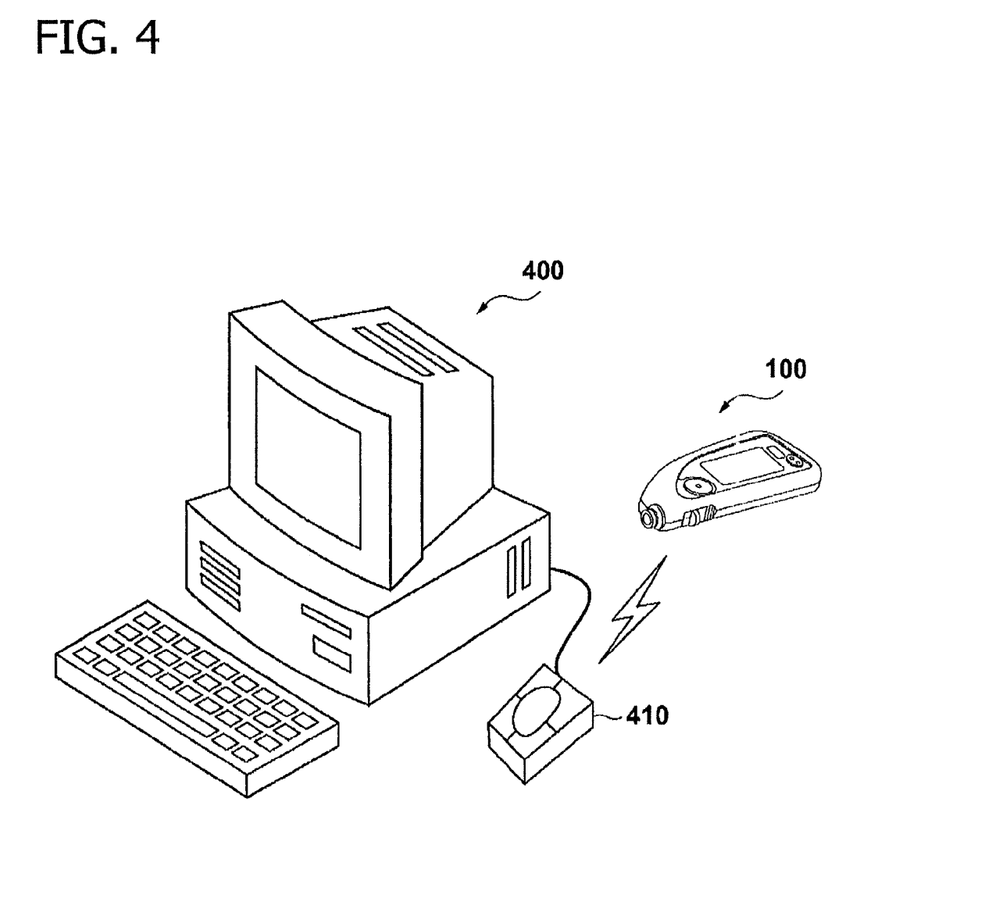
FIG. 4 is a view illustrating a manner in which a static limit value is set by the blood glucose measuring instrument.

A static limit value setting process by the blood glucose measuring instrument 100, information processing terminal and RFID reader/writer is described next with reference to FIGS. 3A, 3B and 4. FIG. 4 illustrates a manner in which the blood glucose measuring instrument 100 is passed over a RFID reader/writer 410 connected to an information processing terminal 400 handled by a doctor or the like in a hospital or the like to set a static limit value to the blood glucose measuring instrument 100. Meanwhile, FIGS. 3A and 3B illustrate the static limit value setting process carried out by the blood glucose measuring instrument 100 and the information processing terminal 400.

In the information processing terminal 400 shown in FIG. 4, an application for setting a static limit value is started (step S321), and if a static limit value is inputted and an identification number of the blood glucose measuring instrument 100 which is to become a setting target of the static limit value is inputted to the information processing terminal 400 by a doctor or the like (step S322), then the RFID reader/writer 410 connected to the information processing terminal 400 starts transmission.

If, in this state, the doctor or the like brings the blood glucose measuring instrument 100 close to the RFID reader/writer 410 (step S301), an antenna coil of the communication section 280 of the blood glucose measuring instrument 100 is excited and electric power is supplied to the communication section 280.

The communication section 280 of the blood glucose measuring instrument 100 starts a communication process in response to supply of power resulting from proximity to the RFID reader/writer 410 (step S302) and transmits an identifier for specifying the blood glucose measuring instrument 100.

The RFID reader/writer 410 which receives the identifier from the communication section 280 of the blood glucose measuring instrument 100 authenticates the blood glucose measuring instrument 100 at step S323 using the identifier. In particular, at step S323, the RFID reader/writer 410 contrasts the identification number inputted by the doctor or the like and the identifier transmitted thereto from the communication section 280 of the blood glucose measuring instrument 100 with each other and permits transmission of a static limit value if they are coincident with each other (i.e., if they match). On the other hand, if they are not coincident with each other, then the RFID reader/writer 410 does not permit transmission of a static limit value.

If transmission of a static limit value is permitted at step S323, then the static limit value inputted at step S322 is transmitted at step S324 by the RFID reader/writer 410. On the other hand, if transmission of a static limit value is not permitted, an error identifier is transmitted by the RFID reader/writer 410.

The blood glucose measuring instrument 100 which receives the static limit value or the error identifier from the RFID reader/writer 410 sets the received static limit value or carries out error display corresponding to the received error identifier on the display section 114 at step S304. The CPU 241 performing step S304 represents an example of a setting means that receives the static limit value (first threshold value information) transmitted by wireless transmission from the information processing terminal (external apparatus) once the information processing terminal has been authenticated and that sets the received static limit value (first threshold value information) as a first threshold value.

After the static limit value is set or the error display is carried out at step S304, the blood glucose measuring instrument 100 advances the processing to step S305, at which it ends the communication process.

On the other hand, the information processing terminal 400 which completes the transmission of a static limit value or an error identifier by the RFID reader/writer 410 advances to the processing to step S325, at which, when transmission of a static limit value is permitted at step S323, it displays that the processing ends normally, but when transmission of a static limit value is not permitted at step S323, it displays that the processing ends with an error.

In this manner, the blood glucose measuring instrument 100 according to the present embodiment is configured such that a value inputted on the information processing terminal 400 by a doctor or the like through the RFID reader/writer 410 connected to the information processing terminal 400 which is handled by the doctor or the like in a hospital or the like is set as a static limit value to the blood glucose measuring instrument 100.

By adopting such a configuration as just described, it becomes possible to set an appropriate static limit value in light of a result of a diagnosis for a patient to the blood glucose measuring instrument 100, and it becomes possible for a doctor or the like to appropriately manage the blood glucose level of the patient. Further, it becomes possible for the patient to make, when a result of measurement exceeding the static limit value is obtained in a later measurement, a decision that the patient should go to the hospital or the like, and delay of treatment by an inappropriate decision of the patient himself or herself can be prevented.

Further, the blood glucose measuring instrument 100 according to the present embodiment is configured such that a static limit value is set by the blood glucose measuring instrument 100 without providing an operation switch or the like for setting a static limit value. Therefore, only a specific person such as a doctor can set a static limit value. Further, a possibility that a subject or the like might rewrite a static limit value by mistake can be prevented.

Though not specifically referenced in the foregoing description, static limit values may be set in response to measurement timings (in short, in response to a classified group illustrated in the table 245 of FIG. 2), or only one static limit value may be set for each patient.

Further, the static limit value may include both of an upper limit value and a lower limit value or may include only an upper limit value or a lower limit value.

The Dynamic Limit Value Setting

Figure 5:
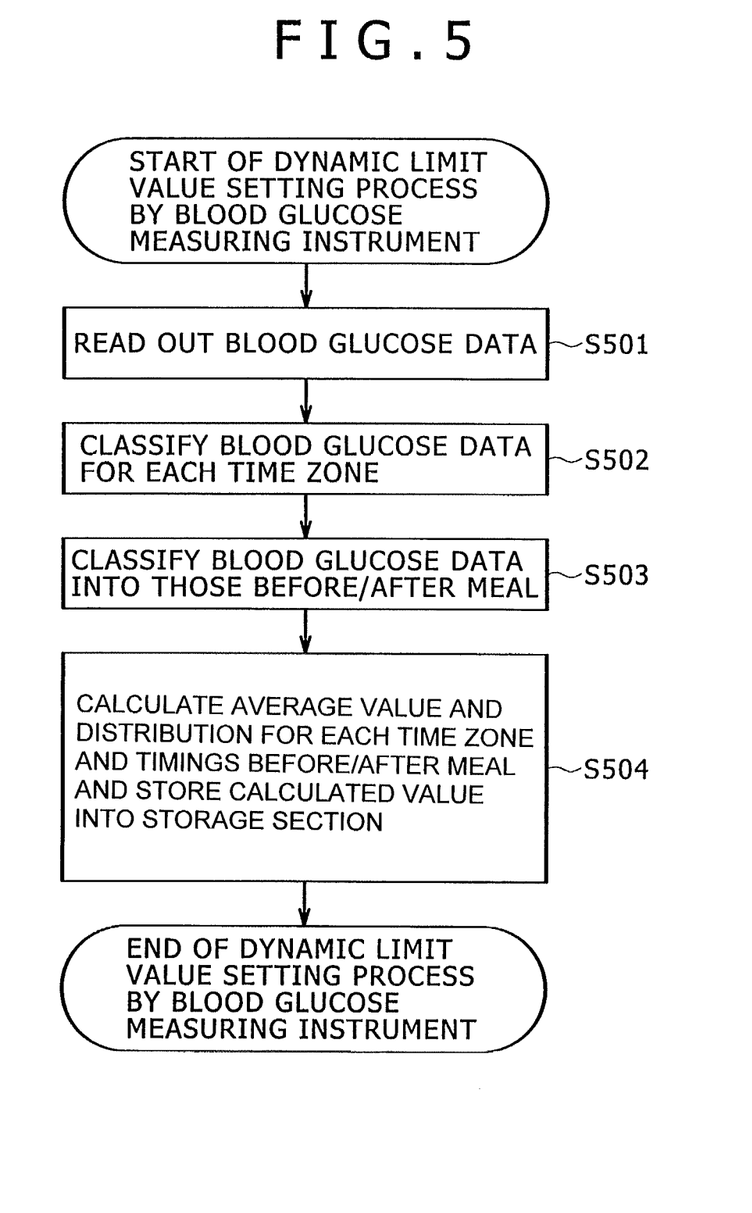
FIG. 5 illustrates an operational routine of a dynamic limit value setting process by the blood glucose measuring instrument.

Setting of the dynamic limit value carried out by the blood glucose measuring instrument 100 is described next with reference to FIG. 5 which illustrates the dynamic limit value setting process.

At step S501, blood glucose level data stored in the storage section 242 are read out, and at step S502, the read out blood glucose level data are classified for individual time zones or periods of time such as the measurement time zones in the table in FIG. 2. Further, at step S503, the blood glucose level data classified according to the time zone are classified into those before a meal and after a meal.

At step S504, an average value and a distribution are calculated for each group based on the blood glucose level data classified at step S503. Further, the calculated distribution is stored as a dynamic limit value (including an upper limit value and a lower limit value) in the group into the storage section 242. The calculation of the distribution is executed when the number of blood glucose level data in each group exceeds a predetermined number. The CPU 241 performing step S504 represents an example of a setting means that calculates, using the blood glucose level data stored in classified groups in the storage section 242, a distribution for each classified group and that sets a dynamic limit value (second threshold value) based on the calculated distribution.

In this manner, the blood glucose measuring instrument 100 according to the present embodiment is configured such that blood glucose level data of a subject in the past are classified into groups for each time zone and for each of timings before and after a meal, and a threshold value is set for each group. Consequently, such a tendency that blood glucose level data acquired by measurement is higher or lower than a blood glucose level in a normal state of a subject himself or herself can be decided appropriately.

Blood Glucose Measurement

Figure 6A:
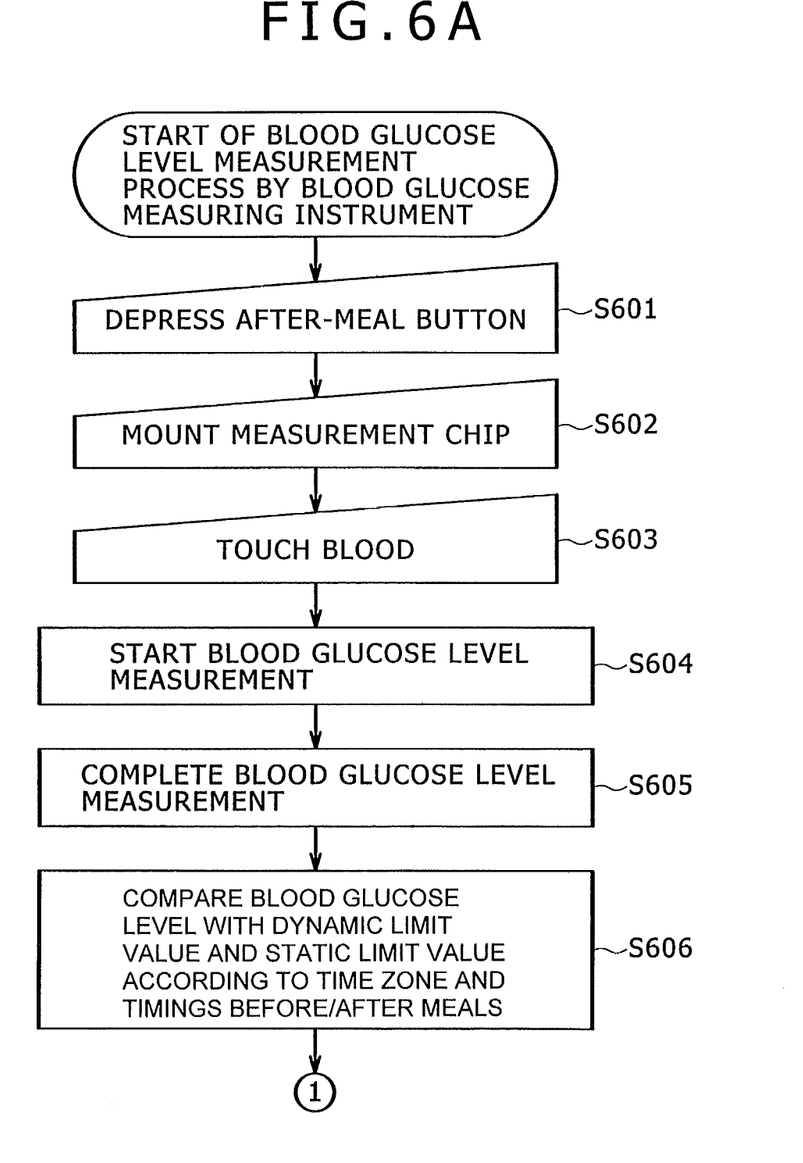
FIG. 6A illustrates a part of an operational routine of a blood glucose level measuring process by the blood glucose measuring instrument.
Figure 6B:
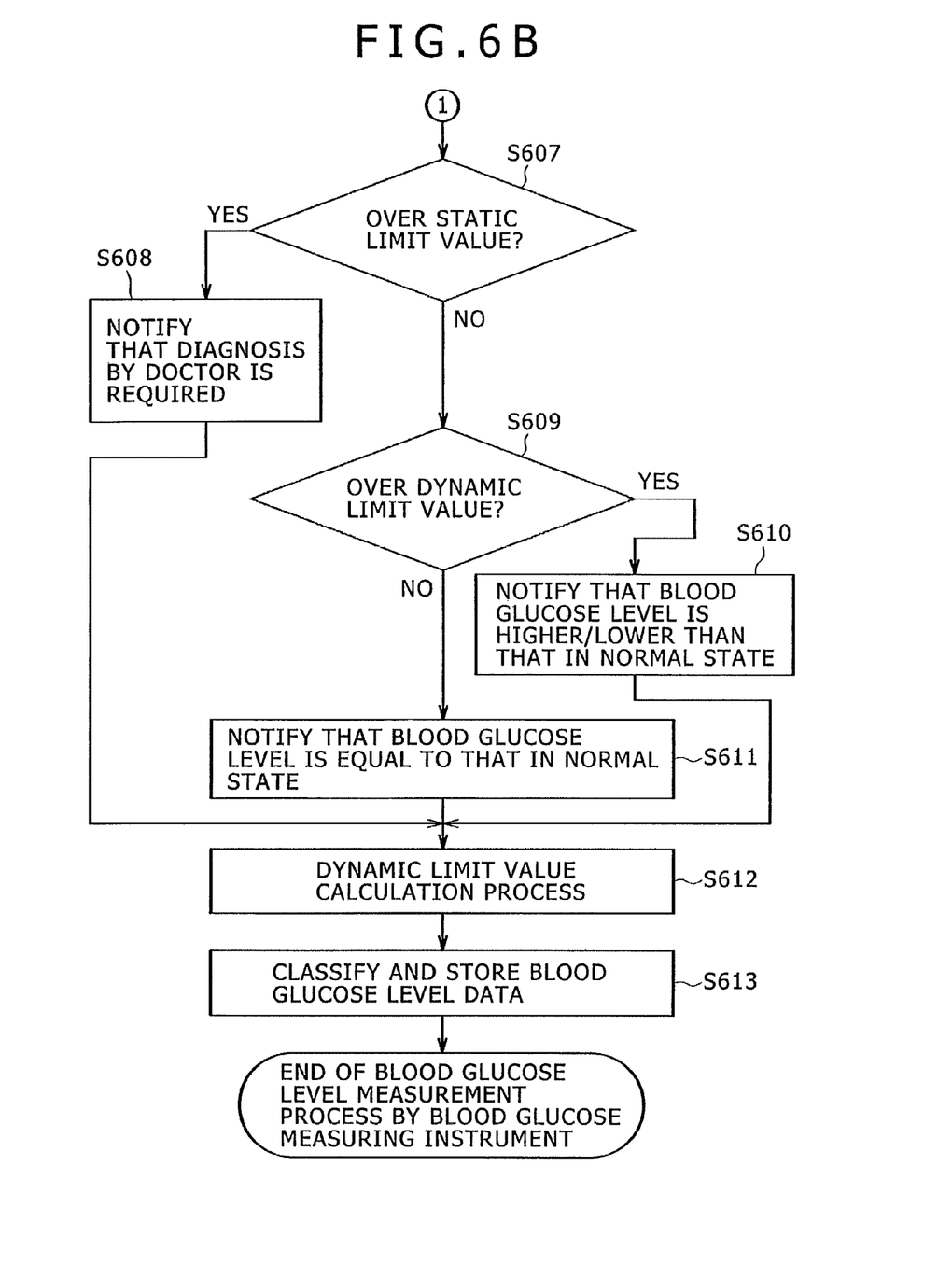
FIG. 6B illustrates another part of an operational routine of the blood glucose level measuring process by the blood glucose measuring instrument.

Blood glucose measurement by the blood glucose measuring instrument 100 is described next with reference to FIGS. 6A and 6B which depict the blood glucose measuring process performed by the blood glucose measuring instrument 100.

At step S601, if the subject depresses the after-meal button 117 upon blood glucose measurement, this operation of the after-meal button 117 is recognized and blood glucose level data acquired in the blood glucose measurement in the present cycle is stored, in the storage section 242, in an associated relationship with an identifier representative of a timing after a meal. On the other hand, if the after-meal button 117 is not depressed at step S601, then the blood glucose level data acquired in the blood glucose measurement in the present cycle is stored, in the storage section 242, in an associated relationship with an identifier representative of a timing before a meal. In short, an identifier indicative of a timing before a meal and an identifier indicative of a timing after a meal are switchably associated in response to the presence or absence of depression of the after-meal button 117. The storage section 242 thus represents an example of storage means for classifying and storing blood glucose level data acquired by blood glucose measurement based on classification according to the measurement timing (i.e., before or after a meal).

Then at step S602, the subject mounts a measuring chip 120 on the measuring instrument main body section 110, and at step S603, the subject touches the blood drop to the measuring chip 120. If the touching to the measuring chip 120 is detected, then the blood glucose measuring instrument 100 starts measurement of the blood glucose level at step S604.

If blood glucose level data is acquired as a result of the measurement started at step S604, then the blood glucose measurement is completed at step S605. At step S606, the time zone within which the blood glucose level measurement has been carried out is identified and it is decided whether or not the after-meal button 117 is depressed at step S601 and then determines whether the blood glucose level measurement has been carried out at a timing before a meal or at another timing after a meal. Then, a static limit value corresponding to the identified time zone and a result of the decision of a timing before or after a meal is read out from the storage section 242 and is compared with the blood glucose level data at step S605. Further, a corresponding dynamic limit value is read out from the storage section 242 and compared with the blood glucose level data at step S605.

If it is decided as a result of the comparison at step S606 that the blood glucose level data at step S605 exceeds the static limit value (i.e., where the decision at step S607 is Yes), the processing advances to step S608.

At step S608, the value of the blood glucose level data is outputted by voice (verbally outputted) to the subject and a voice message that a diagnosis by a doctor is required is outputted.

On the other hand, if it is decided at step S607 that the blood glucose level data at step S605 does not exceed the static limit value (i.e., where the decision at step S607 is No), the processing advances to step S609.

If it is decided at step S609 that the blood glucose level data at step S605 does not exceed the dynamic limit value (i.e., where the decision at step S609 is No), the processing advances to step S611.

At step S611, the value of the blood glucose level data is outputted by voice (verbally outputted) to the subject and a voice message that the blood glucose level data is a blood glucose level in a normal state is outputted.

On the other hand, if it is decided at step S609 that the blood glucose level data at step S605 exceeds the contrasted dynamic limit value (i.e., where the decision at step S609 is Yes), the processing advances to step S610. At step S610, the value of the blood glucose level data is outputted by voice (verbally outputted) to the subject and a voice message that the blood glucose level data is higher (or lower) than that in a normal state is outputted. The CPU 241 performing steps S606-S610 represents an example of notification means that compares the most recently acquired blood glucose level data acquired through blood glucose measurement with the static limit value (first threshold value) and the dynamic limit value (second threshold value) corresponding to the classified group to which the most recently acquired blood glucose level data belongs to and provides notification of the output contents in accordance with a result of the comparison of the most recently acquired blood glucose level data with the static limit value (first threshold value) and the dynamic limit value (second threshold value).

After the voice outputting at step S608, S610 or S611 is completed, at step S612, the blood glucose level data acquired by the blood glucose level measurement process in the present cycle is used to carry out a dynamic limit value calculation process. The details of the dynamic limit value calculation process are described above with reference to FIG. 5, and so a description of the dynamic limit value calculation process is not repeated.

At step S613, the blood glucose level data acquired by the blood glucose level measurement process in the present cycle is stored in an associated relationship with the identifier indicative of a timing after a meal or the identifier indicative of a timing before a meal into the group corresponding to the measurement timing when the measurement is carried out at step S604.

As apparent from the foregoing description, in the blood glucose measuring instrument according to the present embodiment, a subject can recognize a measurement result through voice and can recognize, through voice, an appropriate decision regarding whether or not the measurement result has a level which indicates the necessity for a diagnosis by a doctor or the like. Further, even if the measurement result exhibits a level which indicates no necessity for a diagnosis by a doctor or the like, the subject can recognize whether or not the measurement result is high or low by comparing the measurement result with a blood glucose level in an ordinary state of the subject himself or herself.

In short, with the blood glucose measuring instrument according to the present embodiment, voice guidance allowing a subject to take an appropriate countermeasure is outputted.

In the first embodiment described above, the blood glucose measuring instrument is configured such that a RFID reader/writer is used upon setting of a static limit value. But the blood glucose measuring instrument is not limited in this regard as any other system may be adopted even if it is configured such that a static limit value can be transmitted by wireless transmission.

Further, in the first embodiment described above, the blood glucose measuring instrument is configured such that a voice message is used when a result of a comparison between blood glucose level data and a static limit value or a dynamic limit value (output contents) is to be outputted, the blood glucose measuring instrument is not limited to this. For example, the blood glucose measuring instrument may be configured such that various alarms are used for outputting or may be configured such that characters, figures or the like are displayed for outputting on the display section 114. Or, the blood glucose measuring instrument may be configured such that light emitting elements for emitting light of various colors are provided and are turned on or turned on and off for outputting, or such that a vibrator is provided and is driven to vibrate in various patterns.

The detailed description above describes features and aspects of an embodiment of a blood glucose measuring instrument disclosed by way of example. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A blood glucose measuring instrument comprising:
a communication section configured to wirelessly communicate with an external apparatus operated by a medical professional;
first setting means for setting a received static limit value, inputted by the medical professional at the external apparatus and transmitted wirelessly from the external apparatus to the blood glucose measuring instrument, as a first threshold value;
storage means for storing blood glucose level data acquired by blood glucose measurement of a blood sample taken from a subject, including most recent blood glucose level data acquired by a most recent blood glucose measurement, the storage means storing the blood glucose level data in one of several classified groups each representing a different measurement time period during which blood glucose level measurements were performed;

second setting means for calculating, using the blood glucose level data stored in the classified groups, a dynamic limit value of the blood glucose level data in each classified group and for setting the dynamic limit value as a second threshold value; and notification means which compares the most recent blood glucose level data with both the first threshold value and the second threshold value of the classified group in which the most recent blood glucose level data is classified for providing notification about a result of the comparison of the most recent blood glucose level data with both the first threshold value and the second threshold value of the classified group in which the most recent blood glucose level data is classified.

2. The blood glucose measuring instrument according to claim 1, wherein the notification means is configured to provide voice notification.

3. The blood glucose measuring instrument according to claim 1, wherein the communication section permits wireless communication with the external apparatus only when the external apparatus is authenticated.

4. The blood glucose measuring instrument according to claim 3, further comprising a display and a display controlling section that controls the display to display the most recent blood glucose level and to also display an error message indicating that the external apparatus has not been authenticated.

5. The blood glucose measuring instrument according to claim 3, wherein the notification means outputs a voice message stating that the most recent blood glucose level data represents a change when the most recent blood glucose level data is determined to be outside the second threshold value.

6. The blood glucose measuring instrument according to claim 1, wherein each of the classified groups is a multi-hour measurement timing period constituting a specific part of a twenty-four hour day.

7. The blood glucose measuring instrument according to claim 1, wherein each of the classified groups is either measurement timing before a meal or a measurement timing after a meal.

8. The blood glucose measuring instrument according to claim 1, wherein the classified groups include classified groups each of which is a multi-hour measurement timing period constituting a specific part of a twenty-four hour day, and other classified groups which are either a measurement timing before a meal or a measurement timing after a meal.

9. The blood glucose measuring instrument according to claim 1, further comprising an after-meal button operable to indicate that the blood glucose measurement is occurring after a meal.

10. The blood glucose measuring instrument according to claim 1, wherein the notification means outputs a voice message stating that diagnosis should be made by medical personnel when the most recent blood glucose level data is determined to be higher than the first threshold value.

11. A blood glucose measuring instrument configured to produce voice output, comprising:
   first setting means for receiving first threshold value information transmitted by wireless transmission from an external apparatus in accordance with a condition that the external apparatus has been authenticated and for setting the received first threshold value information as a first threshold value;
   storage means for classifying and storing blood glucose level data acquired by blood glucose measurement based on classification according to the measurement timing;
   second setting means for calculating, using the blood glucose level data stored in classified groups in the storage means, a distribution for each classified group and setting a second threshold value based on the calculated distribution; and
   notification means which compares the blood glucose level data acquired by the blood glucose measurement with the first threshold value and the second threshold value corresponding to the classified group to which the blood glucose level data belongs to notify output contents in accordance with a result of the comparison of the blood glucose level data acquired by the blood glucose measurement with the first threshold value and the second threshold value.

12. The blood glucose measuring instrument according to claim 11, wherein the classified group in accordance with the measurement timing includes a classified group of a time zone within which the blood glucose measurement has been carried out and another classified group indicative of whether the blood glucose measurement has been carried out before or after a meal.

13. The blood glucose measuring instrument according to claim 12, further comprising:
   indication means for providing an indication that the blood glucose measurement has been carried out after a meal, and wherein
   the classified group which indicates whether the blood glucose measurement has been carried out before or after a meal is decided in response to presence or absence of the indication by the indication means.

14. The blood glucose measuring instrument according to claim 13, wherein, when the blood glucose level data acquired by the blood glucose measurement is higher than the first threshold value, the notification means outputs, by voice, a message stating that diagnoses should be performed by a medical professional.

15. The blood glucose measuring instrument according to claim 13, wherein, when the blood glucose level data acquired by the blood glucose measurement is higher than the second threshold value, the notification means outputs, by voice, a massage representing that the blood glucose level data exhibits a change.

16. A method comprising:
   measuring a blood glucose level of a most recent blood sample acquired from a subject though use of a blood glucose measuring instrument;
   comparing the measured blood glucose level of the most recent blood sample to a first threshold value, the first threshold value being a value previously wirelessly received by the blood glucose measurement instrument from an external apparatus at which a medical professional inputted the first threshold value, the blood glucose measurement instrument storing a plurality of past measured blood glucose levels in one of several classified groups, each of the classified groups representing a different measurement time period during which blood glucose level measurements were performed, the measured blood glucose level of the most recent blood sample being classified in one of the classified groups which is the measurement time period during which blood glucose level measurement of the most recent blood sample was performed;
   comparing the measured blood glucose level of the most recent blood sample to a second threshold value of the one classified group, the second threshold value being calculated using the past measured blood glucose levels of the one classified group; and notifying the subject about a result of the comparison of the measured blood glucose level of the most recent blood sample to the first threshold value and the second threshold value.

17. The method according to claim 16, wherein the notifying of the subject includes voice notifying the subject.

18. The method according to claim 16, wherein the notifying of the subject includes notifying the subject whenever the measured blood glucose level of the most recent blood sample exceeds the first threshold value.

19. The method according to claim 16, wherein the notifying of the subject includes notifying the subject whenever the measured blood glucose level of the most recent blood sample exceeds the second threshold value.

20. The method according to claim 16, wherein each of the classified groups is a multi-hour measurement timing period constituting a specific part of a twenty-four hour day, and each of the multi-hour measurement timing periods is further divided into a measurement timing before a meal and a measurement timing after a meal.

* * * * *